United States Patent
Hossainy et al.

[11] Patent Number: 6,153,252
[45] Date of Patent: Nov. 28, 2000

[54] PROCESS FOR COATING STENTS

[75] Inventors: Syed F. A. Hossainy, Edison; Mark B. Roller, North Brunswick; Gerard H. Llanos, Stewartsville; Gregory A. Kopia, Neshanic, all of N.J.

[73] Assignee: Ethicon, Inc., Somerville, N.J.

[21] Appl. No.: 09/294,164

[22] Filed: Apr. 19, 1999

Related U.S. Application Data

[60] Provisional application No. 60/091,217, Jun. 30, 1998.

[51] Int. Cl.$^7$ .............................. A61L 27/00; B05D 7/22
[52] U.S. Cl. ..................... 427/2.3; 427/2.25; 427/2.28; 427/355; 427/235; 427/232
[58] Field of Search ................................. 427/421, 435, 427/355, 409, 235, 2.25, 2.28, 232, 2.3

[56] References Cited

U.S. PATENT DOCUMENTS

| | | |
|---|---|---|
| 3,779,805 | 12/1973 | Alsberg ................................ 117/212 |
| 4,733,665 | 3/1988 | Palmaz . |
| 4,749,585 | 6/1988 | Greco et al. . |
| 4,800,882 | 1/1989 | Gianturco . |
| 4,871,357 | 10/1989 | Hsu et al. . |
| 4,876,109 | 10/1989 | Mayer et al. ............................ 427/2 |
| 4,886,062 | 12/1989 | Wiktor . |
| 5,047,020 | 9/1991 | Hsu . |
| 5,053,048 | 10/1991 | Pinchuk . |
| 5,185,408 | 2/1993 | Tang et al. ............................ 525/415 |
| 5,336,518 | 8/1994 | Narayanan et al. . |
| 5,342,348 | 8/1994 | Kaplan . |
| 5,368,566 | 11/1994 | Crocker . |
| 5,380,299 | 1/1995 | Fearnot et al. . |
| 5,383,853 | 1/1995 | Jung et al. . |
| 5,383,928 | 1/1995 | Scott et al. . |
| 5,403,341 | 4/1995 | Solar . |
| 5,417,969 | 5/1995 | Hsu et al. . |
| 5,443,458 | 8/1995 | Eury . |
| 5,447,724 | 9/1995 | Helmus et al. . |
| 5,454,208 | 10/1995 | Wolf et al. . |
| 5,464,650 | 11/1995 | Berg et al. . |
| 5,569,463 | 10/1996 | Helmus et al. . |
| 5,575,818 | 11/1996 | Pinchuk . |
| 5,591,224 | 1/1997 | Schwartz et al. . |
| 5,616,608 | 4/1997 | Kinsella et al. . |
| 5,632,771 | 5/1997 | Boatman et al. . |
| 5,632,776 | 5/1997 | Kurumatani et al. . |
| 5,632,840 | 5/1997 | Campbell . |
| 5,635,201 | 6/1997 | Fabo ........................................ 424/443 |
| 5,666,728 | 9/1997 | Morris et al. ........................... 514/291 |
| 5,679,400 | 10/1997 | Tuch . |
| 5,691,311 | 11/1997 | Maraganore et al. . |
| 5,697,967 | 12/1997 | Dinh et al. . |
| 5,713,949 | 2/1998 | Jayaraman . |
| 5,716,981 | 2/1998 | Hunter et al. . |
| 5,897,911 | 4/1999 | Loeffler ................................... 427/2.25 |
| 5,922,393 | 7/1999 | Jayaraman .............................. 427/2.3 |

*Primary Examiner*—Shrive Beck
*Assistant Examiner*—Jennifer Kolb

[57] ABSTRACT

A process is provided for coating stents having a first and second surface with passages there between to avoid blockage and bridging of the passages. The process comprises contacting the stent with a liquid coating solution containing a film forming biocompatible polymer under conditions suitable to allow the film forming biocompatible polymer to coat at least one surface of the stent while maintaining a fluid flow through said passages sufficient prevent the film forming biocompatible polymer from substantially blocking said passages. Also described are stents coated by this process.

38 Claims, 5 Drawing Sheets

PROCESS FOR COATING STENTS

FIELD OF THE INVENTION

This application claims benefit from U.S. Provisional Application No. 60/091,217 filed Jun. 30, 1998, which is hereby incorporated by reference herein. The invention relates generally to a process for coating surgical devices. More specifically this invention relates to an improved process for coating stents and the like.

BACKGROUND OF THE INVENTION

Stents, which are generally open tubular structures, have become increasingly important in medical procedures to restore the function of body lumens. Stents are now commonly used in translumenial procedures such as angioplasty to restore an adequate blood flow to the heart. However, stents may stimulate foreign body reactions that result in thrombosis or restenosis. To avoid these complications a variety of stent coatings and compositions have been proposed in the literature both to reduce the incidence of these complications or other complications and restore tissue function by itself or by delivering therapeutic compound to the lumen.

Stents generally are coated by simple dip or spray coating of the stent with polymer or polymer and a pharmaceutical/therapeutic agent or drug. These methods are acceptable for early stent designs that were of open construction fabricated from wires (Wiktor stent) or from ribbons (Gianturco). Dip coating with relatively low coating weights (about 4% polymer) could successfully coat such stents without any problems such as excess coating bridging (i.e. forming a film across) the open space between structural members of the device. This bridging is of particular concern when coating more modern stents that are of less open construction, such as the Palmaz-Schatz, Crown, Multilink or GFX stents. Bridging of the open space (slots) is undesirable because it can interfere with the mechanical performance of the stent, such as expansion during deployment in a vessel lumen. Bridges may rupture upon expansion and provide sites that activate platelet deposition by creating flow disturbances in the adjacent hemodynamic environment or pieces of the bridging film may break off and cause further complications. Bridging of the open slots may also prevent endothelial cell migration complicating the endothelial cell encapsulation of the stent.

Similarly, spray coating can be problematic in that there is a significant amount of spray lost during the process and many of the pharmaceutical agents that one would like to incorporate in the device are quite costly. In addition, in some cases it would be desirable to provide coated stents with high levels of coating and drug. High concentration coatings (~15% polymer with additional drug) are the preferred means to achieve high drug loading. Multiple dip-coating has been described in the literature as a means to build thicker coatings on the stent. However, composition and phase dispersion of the pharmaceutical agents affect sustained release. In addition, the application of multiple dip coats from low concentration solutions often has the effect of reaching a limiting loading level as an equilibrium is reached between the solution concentration and the amount of coating, with or without pharmaceutical agent, deposited on the stent.

SUMMARY OF THE INVENTION

We have discovered a process for coating stents that avoids bridging and allows for preferential coating of stent surfaces. The process comprises contacting a stent having a first and second surface with passages there between with a liquid coating solution containing a film forming biocompatible polymer under conditions suitable to allow the film forming biocompatible polymer to coat at least one surface of the stent while maintaining a fluid flow through said passages sufficient to prevent the film forming biocompatible polymer from substantially blocking said passages.

In a preferred embodiment of the present invention the coating process would comprise placing a tubular stent having a first and second surface with passages there between on a mandrel and contacting the stent and mandrel with a liquid coating solution containing a film forming biocompatible polymer under conditions suitable to allow the film forming biocompatible polymer to coat at least one surface of the stent while moving the stent relative to the mandrel to cause fluid flow through said passages sufficient to prevent the film forming biocompatible polymer from substantially blocking said passages.

In another embodiment of the present invention there is provided a coated stent, comprising a tubular stent having a first and second surface with passages there between, coated with a film-forming biocompatible polymer wherein the polymer coating is greater than 0.5 percent by weight of the coated stent and the passages are not substantially blocked by the bridging of the polymer coating.

DETAILED DESCRIPTION

The present invention provides a process for coating medical devices. The process described herein is well suited to coating medical devices that have passages that may otherwise be blocked or have bridges formed by conventional dip coating. As previously discussed avoiding the formation of bridges is especially important in the coating of perforated structures such as stents. Bridging is a significant problem with stents with passages with a minor dimension less than about 125 mils, especially with passages having a minor dimension smaller than about 50 mils.

Figure 1:
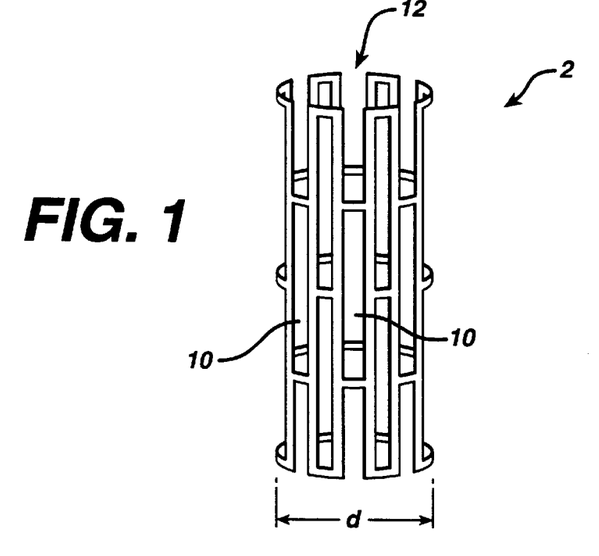
FIG. 1 illustrates a perspective view of a stent prior to coating.

Stents are generally cylindrical and perforated with passages that are slots, ovoid, circular or the like shape. Stents may also be composed of helically wound or serpentine wire structures in which the spaces between the wires form the passages. Stents may be flat perforated structures that are subsequently rolled to form tubular structures or cylindrical structures that are woven, wrapped, drilled, etched or cut to form passages. Examples of stents that may be advantageously coated by the present process include but are not limited stents described in the following U.S. Pat. Nos. 4,733,665 (hereinafter the Palmaz stent which is illustrated in FIG. 1); 4,800,882 (hereinafter the Gianturco stent); 4,886,062 (hereinafter the Wiktor stent) and 5,514,154 (hereinafter the Guidant RX Multilink™ stent). These stents can be made of biocompatible materials including biostable and bioabsorbable materials. Suitable biocompatible metals include, but are not limited to, stainless steel, tantalum, titanium alloys (including nitinol), and cobalt alloys (including cobalt-chromium-nickel alloys). Suitable nonmetallic biocompatible materials include, but are not limited to, polyamides, polyolefins (i.e. polypropylene, polyethylene etc.), nonabsorbable polyesters (i.e. polyethylene terephthalate), and bioabsorbable aliphatic polyesters (i.e. homopolymers and copolymers of lactic acid, glycolic acid, lactide, glycolide, para-dioxanone, trimethylene carbonate, $\epsilon$-caprolactone, etc. and blends thereof).

The present invention utilizes fluid flow or movement through the passages in the perforated medical device to avoid the formation of blockages or bridges. The fluid flow can be provided by active flow systems such as a perforated manifold inserted in the stent to circulate the coating fluid through the passages or can be created by placing the stent on a mandrel or in a small tube that is moved relative to the stent during the coating process to create sufficient fluid flow through the passages and thereby avoid the formation of blockages or bridges.

Figure 2:
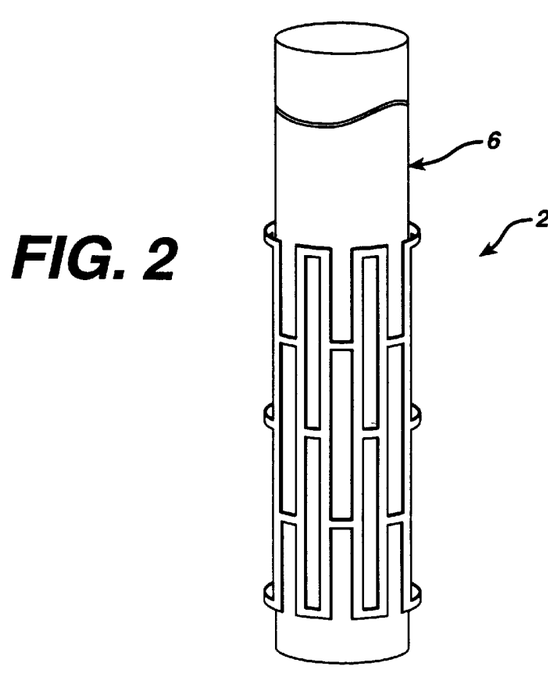
FIG. 2 is a perspective view that illustrates the placement of a stent on a mandrel prior to coating.
Figure 3:
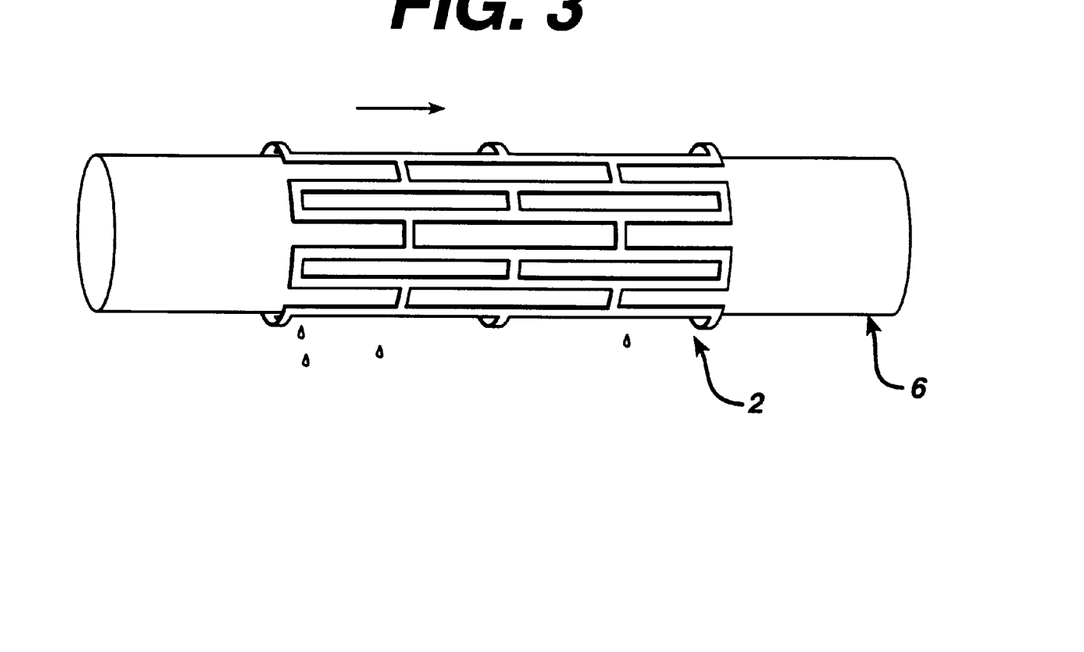
FIG. 3 illustrates the movement of the stent relative to the mandrel in the after removal from the coating bath during the coating process.
Figure 4:
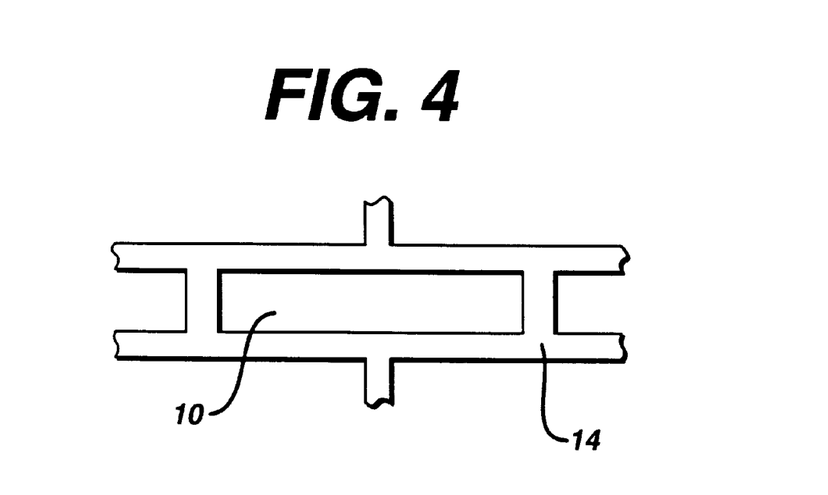
FIG. 4 is an enlarged view of a portion of the coated stent that illustrates the substantial absence of bridging of the stent slots or passages.

In one embodiment of the present invention as illustrated in FIG. 2, a stent 2 is placed over a mandrel 6 that is smaller than the inner diameter d of the stent's intraluminal passage way 12 and dipped into the coating solution. The coated stent is moved relative to the mandrel after it is removed from the coating solution (preferably in one direction). FIG. 3 illustrates the movement of the stent 2 relative to the mandrel 6 after it is removed from bath. The relative outer diameter of the mandrel and inner diameter of the stent are such that after dipping, while the coating is still wet, the movement of the stent along the mandrel's length clears the passages (slots) which remain so on drying. The relative motion of the stent and mandrel, with limited clearance between the stent and mandrel, generates high shear rates which break the surface tension associated with the coating film filling the slots and provides smooth, defect free coating on the stent. Preferably the stent will be moved to an area of the mandrel that has not contacted the coating solution. As is illustrated in FIG. 3 that provides a perspective view of the stent 2 after being coated with coating 14. There are additional advantages: the coatings can be of high concentration and by proper choice of the mandrel diameter to stent diameter (the clearance), the relative thickness of the inner and outer coating of the stent can be controlled. For example, the stent coating can be thicker on the outer surface to contact the luminal wall or thicker on the interior surface to interact with the fluid stream.

The mandrel may be of varying designs (i.e. tapered cones, cylindrical, slotted cylinders, mandrels having cross-sections that are ovoid, triangular or polygonal and would include shafts with veins or paddles). Additionally, the movement of the mandrel relative to the stent may not only be laterally, but may also consist of rotational movement. Object of the mandrel design being to assure sufficient shear flow relative to the passages to insure that the passages do not be come blocked.

Film-forming polymers that can be used for coatings in this application can be absorbable or non-absorbable and must be biocompatible to minimize irritation to the vessel wall. The polymer may be either biostable or bioabsorbable depending on the desired rate of release or the desired degree of polymer stability, but a bioabsorbable polymer is preferred since, unlike biostable polymer, it will not be present long after implantation to cause any adverse, chronic local response. Furthermore, bioabsorbable polymers do not present the risk that over extended periods of time there could be an adhesion loss between the stent and coating caused by the stresses of the biological environment that could dislodge the coating and introduce further problems even after the stent is encapsulated in tissue.

Suitable film-forming bioabsorbable polymers that could be used include polymers selected from the group consisting of aliphatic polyesters, poly(amino acids), copoly(ether-esters), polyalkylenes oxalates, polyamides, poly (iminocarbonates), polyorthoesters, polyoxaesters, polyamidoesters, polyoxaesters containing amido groups, poly(anhydrides), polyphosphazenes, biomolecules and blends thereof. For the purpose of this invention aliphatic polyesters include homopolymers and copolymers of lactide (which includes lactic acid d-,l- and meso lactide), $\epsilon$-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, 6,6-dimethyl-1,4-dioxan-2-one and polymer blends thereof. Poly(iminocarbonate) for the purpose of this invention include as described by Kemnitzer and Kohn, in the *Handbook of Biodegradable Polymers,* edited by Domb, Kost and Wisemen, Hardwood Academic Press, 1997, pages 251–272. Copoly(ether-esters) for the purpose of this invention include those copolyester-ethers described in Journal of Biomaterials Research, Vol. 22, pages 993–1009, 1988 by Cohn and Younes and Cohn, Polymer Preprints (ACS Division of Polymer Chemistry) Vol. 30(1), page 498, 1989 (e.g. PEO/PLA). Polyalkylene oxalates for the purpose of this invention include U.S. Pat. Nos. 4,208,511; 4,141,087; 4,130,639; 4,140,678; 4,105, 034; and 4,205,399 (incorporated by reference herein). Polyphosphazenes, co-, ter- and higher order mixed monomer based polymers made from L-lactide, D,L-lactide, lactic acid, glycolide, glycolic acid, para-dioxanone, trimethylene carbonate and $\epsilon$-caprolactone such as are described by Allcock in *The Encyclopedia of Polymer Science,* Vol. 13, pages 31–41, Wiley Intersciences, John Wiley & Sons, 1988 and by Vandorpe, Schacht, Dejardin and Lemmouchi in the *Handbook of Biodegradable Polymers,* edited by Domb, Kost and Wisemen, Hardwood Academic Press, 1997, pages 161–182 (which are hereby incorporated by reference herein). Polyanhydrides from diacids of the form HOOC—$C_6H_4$—O—$(CH_2)_m$—O—$C_6H_4$—COOH where m is an integer in the range of from 2 to 8 and copolymers thereof with aliphatic alpha-omega diacids of up to 12 carbons. Polyoxaesters polyoxaamides and polyoxaesters containing amines and/or amido groups are described in one or more of the following U.S. Pat. Nos. 5,464,929; 5,595,751; 5,597, 579; 5,607,687; 5,618,552; 5,620,698; 5,645,850; 5,648, 088; 5,698,213 and 5,700,583; (which are incorporated herein by reference). Polyorthoesters such as those described by Heller in *Handbook of Biodegradable Polymers,* edited by Domb, Kost and Wisemen, Hardwood Academic Press, 1997, pages 99–118 (hereby incorporated herein by reference). Film-forming polymeric biomolecules for the purpose of this invention include naturally occurring materials that may be enzymatically degraded in the human body or are hydrolytically unstable in the human body such as fibrin, fibrinogen, collagen, elastin, and absorbable biocompatable polysaccharides such as chitosan, starch, fatty acids (and esters thereof), glucoso-glycans and hyaluronic acid.

Suitable film-forming biostable polymers with relatively low chronic tissue response, such as polyurethanes, silicones, poly(meth)acrylates, polyesters, polyalkyl oxides (polyethylene oxide), polyvinyl alcohols, polyethylene glycols and polyvinyl pyrrolidone, as well as, hydrogels such as those formed from crosslinked polyvinyl pyrrolidinone and polyesters could also be used. Other polymers could also be used if they can be dissolved, cured or polymerized on the stent. These include polyolefins, polyisobutylene and etheylene-alphaolefin copolymers; acrylic polymers (including methacrylate) and copolymers, vinyl halide polymers and copolymers, such as polyvinyl chloride; polyvinyl ethers, such as polyvinyl methyl ether; polyvinylidene halides such as polyvinylidene fluoride and polyvinylidene chloride; polyacrylonitrile, polyvinyl ketones; polyvinyl aromatics such as polystyrene; polyvinyl esters such as polyvinyl acetate; copolymers of vinyl monomers with each other and olefins, such as etheylene-methyl methacrylate copolymers, acrylonitrile-styrene copolymers, ABS resins and ethylene-vinyl acetate copolymers; polyamides,such as Nylon 66 and polycaprolactam; alkyd resins; polycarbonates; polyoxymethylenes; polyimides; polyethers; epoxy resins, polyurethanes; rayon; rayon-triacetate, cellulose, cellulose acetate, cellulose acetate butyrate; cellophane; cellulose nitrate; cellulose propionate; cellulose ethers (i.e. carboxymethyl cellulose and hydoxyalkyl celluloses); and combinations thereof. Polyamides for the purpose of this application would also include polyamides of the form —NH—$(CH_2)_n$—CO— and NH—$(CH_2)_x$—NH—CO—$(CH_2)_y$—CO, wherein n is preferably an integer in from 6 to 13; x is an integer in the range of form 6 to 12; and y is an integer in the range of from 4 to 16. The list provided above is illustrative but not limiting.

The polymers used for coatings must be film-forming polymers that have molecular weight high enough as to not be waxy or tacky. The polymers also must adhere to the stent and not be so readily deformable after deposition on the stent as to be able to be displaced by hemodynamic stresses. The polymers molecular weight be high enough to provide sufficient toughness so that the polymers will not to be rubbed off during handling or deployment of the stent and must not crack during expansion of the stent. The melting point of the polymer used in the present invention should have a melting temperature above 40° C., preferably above about 45° C., more preferably above 50° C. and most preferably above 55° C.

The preferable coatings to use for this application are bioabsorbable elastomers, more preferably aliphatic polyester elastomers. In the proper proportions aliphatic polyester copolymers are elastomers. Elastomers present the advantage that they tend to adhere well to the metal stents and can withstand significant deformation without cracking. The high elongation and good adhesion provide superior performance to other polymer coatings when the coated stent is expanded. Examples of suitable bioabsorbable elastomers are described in U.S. Pat. No. 5,468,253 hereby incorporated by reference. Preferably the bioabsorbable biocompatible elastomers based on aliphatic polyester, including but not limited to those selected from the group consisting of elastomeric copolymers of ε-caprolactone and glycolide (preferably having a mole ratio of ε-caprolactone to glycolide of from about 35:65 to about 65:35, more preferably 45:55 to 35:65) elastomeric copolymers of ε-caprolactone and lactide, including L-lactide, D-lactide blends thereof or lactic acid copolymers (preferably having a mole ratio of ε-caprolactone to lactide of from about 35:65 to about 90:10 and more preferably from about 35:65 to about 65:35 and most preferably from about 45:55 to 30:70 or from about 90:10 to about 80:20) elastomeric copolymers of p-dioxanone (1,4-dioxan-2-one) and lactide including L-lactide, D-lactide and lactic acid (preferably having a mole ratio of p-dioxanone to lactide of from about 40:60 to about 60:40) elastomeric copolymers of ε-caprolactone and p-dioxanone (preferably having a mole ratio of ε-caprolactone to p-dioxanone of from about 30:70 to about 70:30) elastomeric copolymers of p-dioxanone and trimethylene carbonate (preferably having a mole ratio of p-dioxanone to trimethylene carbonate of from about 30:70 to about 70:30), elastomeric copolymers of trimethylene carbonate and glycolide (preferably having a mole ratio of trimethylene carbonate to glycolide of from about 30:70 to about 70:30), elastomeric copolymer of trimethylene carbonate and lactide including L-lactide, D-lactide, blends thereof or lactic acid copolymers (preferably having a mole ratio of trimethylene carbonate to lactide of from about 30:70 to about 70:30) and blends thereof. As is well known in the art these aliphatic polyester copolymers have different hydrolysis rates, therefore, the choice of elastomer may in part be based on the requirements for the coatings adsorption. For example ε-caprolactone-co-glycolide copolymer (45:55 mole percent, respectively) films lose 90% of their initial strength after 2 weeks in simulated physiological buffer whereas the ε-caprolactone-co-lactide copolymers (40:60 mole percent, respectively) loses all of its strength between 12 and 16 weeks in the same buffer. Mixtures of the fast hydrolyzing and slow hydrolyzing polymers can be used to adjust the time of strength retention.

The preferred bioabsorbable elastomeric polymers should have an inherent viscosity of from about 1.0 dL/g to about 4 dL/g, preferably an inherent viscosity of from about 1.0 dL/g to about 2 dL/g and most preferably an inherent viscosity of from about 1.2 dL/g to about 2 dL/g as determined at 25° C. in a 0.1 gram per deciliter (g/dL) solution of polymer in hexafluoroisopropanol (HFIP).

The solvent is chosen such that there is the proper balance of viscosity, deposition level of the polymer, solubility of the pharmaceutical agent, wetting of the stent and evaporation rate of the solvent to properly coat the stents. In the preferred embodiment, the solvent is chosen such the pharmaceutical agent and the polymer are both soluble in the solvent. In some cases, the solvent must be chosen such that the coating polymer is soluble in the solvent and such that pharmaceutical agent is dispersed in the polymer solution in the solvent. In that case the solvent chosen must be able to suspend small particles of the pharmaceutical agent without causing them to aggregate or agglomerate into collections of particles that would clog the slots of the stent when applied. Although the goal is to dry the solvent completely from the coating during processing, it is a great advantage for the solvent to be non-toxic, non-carcinogenic and environmentally benign. Mixed solvent systems can also be used to control viscosity and evaporation rates. In all cases, the solvent must not react with or inactivate the pharmaceutical agent or react with the coating polymer. Preferred solvents include by are not limited to: acetone, N-methylpyrrolidone (NMP), dimethyl sulfoxide (DMSO), toluene, methylene chloride, chloroform, 1,1,2-trichloroethane (TCE), various freons, dioxane, ethyl acetate, tetrahydrofuran (THF), dimethylformamide (DMF), and dimethylacetamide (DMAC).

The film-forming biocompatible polymer coatings are generally applied to reduce local turbulence in blood flow through the stent, as well as, adverse tissue reactions. The coating may also be used to administer a pharmaceutically active material to the site of the stents placement. Generally, the amount of polymer coating to be placed on the stent will vary with the polymer and the stent design and the desired effect of the coating. As a guideline the amount of coating may range from about 0.5 to about 20 as a percent of the total weight of the stent after coating and preferably will range from about 1 to about 15 percent. The polymer coatings may be applied in one or more coating steps depending on the amount of polymer to be applied. Different polymers may also be used for different layers in the stent coating. In fact it is highly advantageous to use a dilute first coating solution as primer to promote adhesion of a subsequent coating layers that may contain pharmaceutically active materials.

Additionally, a top coating can be applied to delay release of the pharmaceutical agent, or they could be used as the matrix for the delivery of a different pharmaceutically active material. The amount of top coatings on the stent may vary, but will generally be less than about 2000 $\mu$g, preferably the amount of top coating will be in the range of about 10 $\mu$g to about 1700 $\mu$g and most preferably in the range of from about 300 $\mu$g to about 1600 $\mu$g. Layering of coating of fast and slow hydrolyzing copolymers can be used to stage release of the drug or to control release of different agents placed in different layers. Polymer blends may also be used to control the release rate of different agents or to provide desirable balance of coating (i.e. elasticity, toughness etc.) and drug delivery characteristics (release profile). Polymers with different solubilities in solvents can be used to build up different polymer layers that may be used to deliver different drugs or control the release profile of a drug. For example since $\epsilon$-caprolactone-co-lactide elastomers are soluble in ethyl acetate and $\epsilon$-caprolactone-co-glycolide elastomers are not soluble in ethyl acetate. A first layer of $\epsilon$-caprolactone-co-glycolide elastomer containing a drug can be over coated with $\epsilon$-caprolactone-co-glycolide elastomer using a coating solution made with ethyl acetate as the solvent. Additionally, different monomer ratios within a copolymer, polymer structure or molecular weights may result in different solubilities. For example, 45/55 $\epsilon$-caprolactone-co-glycolide at room temperature is soluble in acetone whereas a similar molecular weight copolymer of 35/65 $\epsilon$-caprolactone-co-glycolide is substantially insoluble within a 4 weight percent solution. The second coating (or multiple additional coatings) can be used as a top coating to delay the drug deliver of the drug contained in the first layer. Alternatively, the second layer could contain a different drug to provide for sequential drug delivery. Multiple layers of different drugs could be provided by alternating layers of first one polymer then the other. As will be readily appreciated by those skilled in the art numerous layering approaches can be used to provide the desired drug delivery.

The coatings can be used to deliver therapeutic and pharmaceutic agents such as, but not limited to: antiproliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which don't have the capacity to synthesize their own asparagine); antiproliferative/antimitotic alkylating agents such as nitrogen mustards(mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin),trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine{cladribine}); platinum coordination complexes (cisplatin, carboplatin), procarbazine, hydroxyurea, mitotane, aminoglutethimide; hormones (i.e. estrogen); Anticoaglants (heparin, synthetic heparin salts and other inhibitors of thrombin); fibrinolytic agents (such as tissue plasminogen activator, streptokinase and urokinase); antiplatelet: (aspirin, dipyridamole, ticlopidine, clopidogrel, abciximab); antimigratory; antisecretory (breveldin); antiinflammatory: such as adrenocortical steroids (cortisol, cortisone, fludrocortisone, prednisone, prednisolone, 6$\alpha$-methylprednisolone, triamcinolone, betamethasone, and dexamethasone), non-steroidal agents (salicylic acid derivatives i.e. aspirin; para-aminophenol derivatives i.e. acetominophen; Indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressive: (cyclosporine, tacrolimus (FK-506), sirolimus (rapamycin), azathioprine, mycophenolate mofetil); Angiogenic: vascular endothelial growth factor (VEGF), fibroblast growth factor (FGF); nitric oxide donors; anti-sense olgio nucleotides and combinations thereof.

Coating may be formulated by mixing one or more therapeutic agents with the coating polymers in a coating mixture. The therapeutic agent may be present as a liquid, a finely divided solid, or any other appropriate physical form. Optionally, the mixture may include one or more additives, e.g., nontoxic auxiliary substances such as diluents, carriers, excipients, stabilizers or the like. Other suitable additives may be formulated with the polymer and pharmaceutically active agent or compound. For example hydrophilic polymers selected from the previously described lists of biocompatible film forming polymers may be added to a biocompatible hydrophobic coating to modify the release profile (or a hydrophobic polymer may be added to a hydrophilic coating to modify the release profile). One example would be adding a hydrophilic polymer selected from the group consisting of polyethylene oxide, polyvinyl pyrrolidone, polyethylene glycol, carboxylmethyl cellulose, hydroxymethyl cellulose and combination thereof to an aliphatic polyester coating to modify the release profile. Appropriate relative amounts can be determined by monitoring the in vitro and/or in vivo release profiles for the therapeutic agents.

The best conditions for the coating application are when the polymer and pharmaceutic agent have a common solvent. This provides a wet coating that is a true solution. Less desirable, yet still usable are coatings that contain the pharmaceutic as a solid dispersion in a solution of the polymer in solvent. Under the dispersion conditions, care must be taken to ensure that the particle size of the dispersed pharmaceutical powder, both the primary powder size and its aggregates and agglomerates, is small enough not to cause an irregular coating surface or to clog the slots of the stent that we need to keep coating-free. In cases where a dispersion is applied to the stent and we want to improve the smoothness of the coating surface or ensure that all particles of the drug are fully encapsulated in the polymer, or in cases where we may want to slow the release rate of the drug, deposited either from dispersion or solution, we can apply a clear (polymer only) top coat of the same polymer used to provide sustained release of the drug or another polymer that further restricts the diffusion of the drug out of the coating. The top coat can be applied by dip coating with mandrel as previously described or by spray coating (loss of coating during spray application is less problematic for the clear topcoat since the costly drug is not included). Dip coating of the top coat can be problematic if the drug is more soluble in the coating solvent than the polymer and the clear coating redissolves previously deposited drug. The time spent in the dip bath may need to be limited so that the drug is not extracted out into the drug-free bath. Drying should be rapid so that the previously deposited drug does not completely diffuse into the topcoat.

The amount of therapeutic agent will be dependent upon the particular drug employed and medical condition being treated. Typically, the amount of drug represents about 0.001% to about 70%, more typically about 0.001% to about 60%, most typically about 0.001% to about 45% by weight of the coating.

The quantity and type of polymers employed in the coating layer containing the pharmaceutic agent will vary depending on the release profile desired and the amount of drug employed. The product may contain blends of the same or different polymers having different molecular weights to provide the desired release profile or consistency to a given formulation.

Absorbable polymers upon contact with body fluids including blood or the like, undergoes gradual degradation (mainly through hydrolysis) with concomitant release of the dispersed drug for a sustained or extended period (as compared to the release from an isotonic saline solution). Non-absorbable and absorbable polymers may release dispersed drug by diffusion. This can result in prolonged delivery (over, say 1 to 2,000 hours, preferably 2 to 800 hours) of effective amounts (say, 0.001 $\mu g/cm^2$-min to 100 $\mu g/cm^2$-min) of the drug. The dosage can be tailored to the subject being treated, the severity of the affliction, the judgment of the prescribing physician, and the like.

Individual formulations of drugs and polymers may be tested in appropriate in vitro and in vivo models to achieve the desired drug release profiles. For example, a drug could be formulated with a polymer (or blend) coated on a stent and placed in an agitated or circulating fluid system (such as PBS 4% bovine albumin). Samples of the circulating fluid could be taken to determine the release profile (such as by HPLC). The release of a pharmaceutical compound from a stent coating into the interior wall of a lumen could be modeled in appropriate porcine system. The drug release profile could then be monitored by appropriate means such as, by taking samples at specific times and assaying the samples for drug concentration (using HPLC to detect drug concentration). Thrombus formation can be modeled in animal models using the $^{111}$In-platelet imaging methods described by Hanson and Harker, Proc. Natl. Acad. Sci. USA 85:3184–3188 (1988). Following this or similar procedures, those skilled in the art will be able to formulate a variety of stent coating formulations.

EXAMPLE 1

An absorbable elastomer based on 45:55 mole percent copolymer of ε-caprolactone and glycolide, with an IV of 1.58 (0.1 g/dl in hexafluoroisopropanol[HFIP] at 25° C.) was dissolved five percent (5%) by weight in acetone and separately fifteen percent (15%) by weight in 1,1,2-trichloroethane. The synthesis of the elastomer is described in U.S. Pat. No. 5,468,253 incorporated herein by reference. Gentle heating can be used to increase the dissolution rate. The high concentration coating could be formulated with or without pharmaceutical agent present. An initial primer coat of only the polymer is put on Cordis P-S 153 stent (commercially available from Cordis, a Johnson & Johnson Company) by dip coating in the five percent (5%) solution while the stent is placed on a 0.032 inch (0.81 mm) diameter mandrel. The mandrel, with the stent on it, is removed from the dip bath and before the coating has a chance to dry the stent is moved along the length on the mandrel in one direction. This wiping motion applies high shear to the coating trapped between the stent and the mandrel. The high shear rate forces the coating out through the slots cut into the tube from which the stent is formed. This wiping action serves to force the coating out of the slots and keeps them clear. The "primed stent" is allowed to air dry at room temperature. The prime coat is about 100 micrograms of coating. After 1–2 hours of air drying, the stent is remounted on a 0.0355 inch (0.9 mm) clean mandrel and dipped into a second, concentrated coat solution. This can be drug free or can contain about six percent (6%) by weight drug in addition to about fifteen percent (15%) polymer by weight in the coating solution. The dip and wipe process is repeated. The final coated stent is air dried for 12 hours and then put in a 60° C. vacuum oven (at 30 in Hg vacuum) for 24 hours to dry. This method provides a coated stent with about 270 micrograms of polymer and about 180 micrograms of drug.

EXAMPLE 2

This example describes experiments that demonstrate the ability of the dip and wipe coating approach to incorporate a bioactive agent in the coating and that the bioactive agent retains its biological activity. An initial primer coat of only the polymer described in Example 1 was placed on Cordis P-S 153 stent by dip coating in the five percent (5%) solution by weight while the stent is placed on a 0.032 inch (0.81 mm) diameter mandrel. And primed as described in Example 1. The coated stent was then coated a second time with a coating solution of polymer and drug. The coated stent was dipped and wipe coated using the mandrel and a high concentration drug-polymer (15% polymer, 1:100 drug:polymer, and 2000 U/ml heparin-benzalkonium chloride [HBAC]; all in 70/30 acetone/DMSO) solution by the method described in Example 1. The HBAC coated stents had a total coating weight of about 350 micrograms. Coated stents were sent to North American Science Assocites Inc. (Northwood, Ohio U.S.A.) for a standard rabbit whole blood clotting time assay. The assay was performed by placing the stents on the surface of the Tryptic Soy Agar (TSA) plate along with a negative control sample (glass tubing) and a positive control (HBAC coated glass tubing). The 15×150 mm TSA plate was flooded with 35 ml of whole rabbit blood, obtained by arterial draw of a euthanized rabbit. The test plate was incubated in ambient room temp. For 20–40 minutes. Following the incubation period, the samples were removed from the thrombus formed in the plate using forceps. The test and control sections were observed for evidence of adherence to the thrombus formation upon removal.

The heparinized stents were proven to be nonthrombogenic as compared with the non-heparinized controls.

EXAMPLE 3

Figure 5:
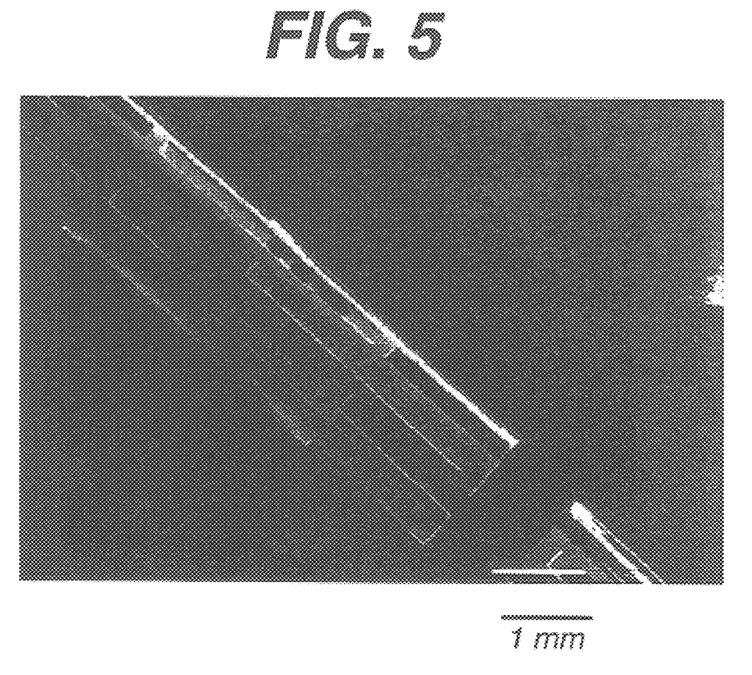
FIG. 5 is a pictomicrograph that illustrates a stent that has been coated by conventional dip coating process with about a 4 weight percent coating solution.
Figure 6:
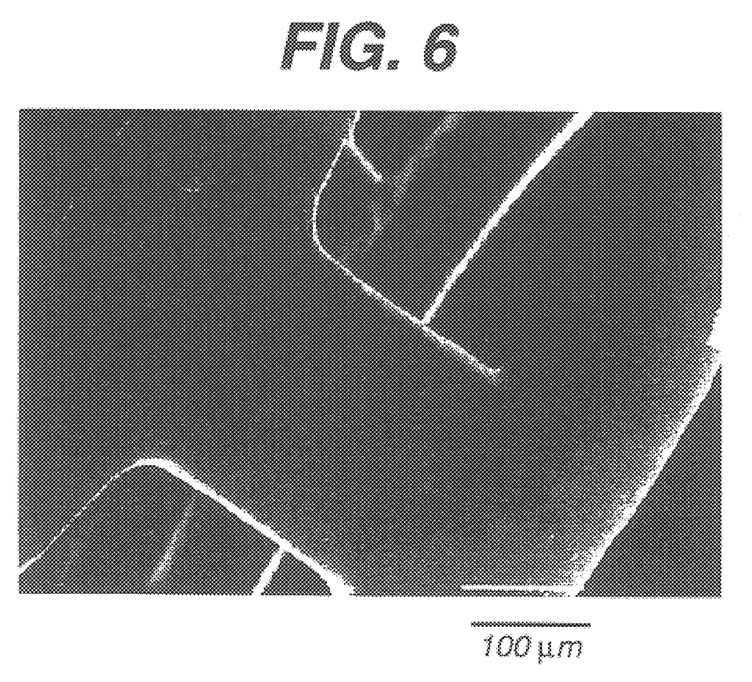
FIG. 6 is a pictomicrograph that illustrate a stent that has been coated by the inventive coating process with about a 13 weight percent coating solution.

This example describes experiments that demonstrate the ability of the dip and wipe coating approach to provide coated stent with high coating loading and no bridging of the slots in the stent. A Cordis P-S 153 stent was taken and dip coated into a five percent (5%) solution of the elastomeric 45:55 mole percent of ε-caprolactone and glycolide copolymer (IV=1.58) described in Example 1. The stent was removed and allow to air dry for 1–2 hours at room temperature. The coating added to the stent was about 100–150 micrograms. The slots in the stent were bridged with dry coating film (FIG. 5). A second Cordis P-S 153 was dipped and wipe coated with the coating solution containing fifteen percent (15%) polymer as described in Example 1. The stent was found to have slots free of coating and to be loaded with 300 micrograms of coating. Similar experiments were performed with the Cordis Crown™ stent, the Guidant RX Multilink™ stent and the AVE GFX ™stent. The results were identical, dipping and wipping over a mandril allows high concentration coatings to provide high coating build on a variety of stents without the adverse effect of bridging the slots.

EXAMPLE 4

This example demonstrates the differential solubility of elastomeric ε-caprolactone and glycolide copolymers and elastomeric ε-caprolactone and lactide copolymers in ethyl acetate. 0.2 g of ε-caprolactone and glycolide copolymer (45/55, IV=1.5, Tm ~62° C.) were placed in a flat bottom glass vial along with 4 grams of ethyl acetate. These were heated to about 50° C. on a hot plate with stirring bar over night. The result was partial solution with clear polymer on the walls and a cloudy solution at 50° C. but the polymer precipitated out and coated the walls of the vial when the temperature came back to room temperature (~25° C). Similarly, 0.2 g of ε-caprolactone and lactide copolymer (40/60, IV=1.5, Tm ~132° C.) were placed in a flat bottom glass vial with 4 g of ethyl acetate made in a manner similar to that described in Example 11. These were heated to about 50° C. on a hot plate with stirring bar over night. The particles first swelled and then went into solution. On cooling to room temperature the solution remained clear and uniform.

EXAMPLE 5
Multiple Dipping

P-S stents were coated from a 5% w/w 45:55 ε-caprolactone and glycolide solution as described in the example 1. The initial coating resulted in ~100 micrograms of total solid on the stent. The stents were dried and then coated from a 15% w/w 45:55 ε-caprolactone and glycolide and 6% w/w drug solution. The second step resulted in ~170 micrograms of total solid and ~60 micrograms of drug on the stent. Stents were coated again from the same second solution and an increment of 30 micrograms (a total of 200 micrograms) of total solid and an increment of 20 micrograms of drug (a total of 80 micrograms) was observed. However when the dried stents were coated again with the same second solution total weight gain of the solid and the drug remain same.

EXAMPLE 6

This Example describes applying a top coating to a coated stent with an ultrasonic spraying device.

A five percent by weight coating solution is made using 45:55 ε-caprolactone and glycolide described in Example 1 in a solvent solution of TCE:Acetone (1:1, w/w)

The ultrasonic spray unit is composed of a SonoTek (New York, U.S.A.) broadband ultrasonic generator (model 60-05108) attached to a nozzle (model 06-04010) an oscillated at 60 KHz to generate a mean droplet size of 31 microns. The power at which the system was operated was is 5.8 mWatts. The flow rate was adjusted to about 0.3 ml/min. The ultrasonic spray system was placed in a plastic bag containment system to eliminate air currents and to slow evaporation. Stents would be positioned 1.5–5 cm distance from the nozzle and had a dwell time in the spray cloud of about 15–40 seconds.

The stent would then be dried in ambient conditions for 18–24 hours and subsequently vacuum dried at 60° C. for 24 hours. Approximately, 100–150 micrograms of polymer was deposited per top coating run. A mandrel can be used to prevent coating the inside of the stent if desired.

EXAMPLE 7

This Example describes the preparation of coated stents containing various levels of rapamycin for in vitro drug release testing.

0.06 gms of Rapamycin was dissolved into 0.8 gms of 15% CAP/GLY solution in 1,1,2 TCE. The resulting coating solution contained 33.3% w/w drug on a dry, solid-only basis. Stents were coated by the method described in Example 1 and the coated stents were designated as 'Std 33%'.

0.015 gms of Rapamycin was dissolved into 0.5 gms of 18% CAP/GLY solution in 1,1,2 TCE. The resulting coating solution contained 14.3% w/w drug on a dry, solid-only basis. Stents were coated by the method described in Example 1 and the coated stents were designated as '14%'

0.028 gms of rapamycin was dissolved into 0.5 gm of 18% CAP/GLY solution in 1,1,2 TCE. The resulting coating solution contained 23.7% w/w drug on a dry, solid-only basis. Stents were coated by the method described in Example 1. The dip-coated stents were spray coated with polymer-only solution as described in Example 6. The final coated stents were designated as '24-TC%'

0.028 gms of rapamycin was dissolved into 0.5 gm of 18% CAP/GLY solution in 1,1,2 TCE. The resulting coating solution contained 23.7% w/w drug on a dry, solid-only basis. Stents were coated by the method described in Example 1. The dip-coated stents were spray coated with polymer-only solution as described in Example 6;

However, a total volume of 200 microliters of spray solution was used in this case. The final coated stents were designated as '24-Thick TC%'

0.06 gms of rapamycin was dissolved into 0.8 gm of 15% CAP/GLY solution in 1,1,2 TCE. The resulting coating solution contained 33.3% w/w drug on a dry, solid-only basis. Stents were coated by the method described in Example 1. The dip-coated stents were spray coated twice with ε-caprolactone-co-lactide (Cap/Lac) solution as described in Example 4. The final coated stents were designated as '33-TC%'.

0.06 gms of rapamycin was dissolved into 0.8 gm of 15% CAP/LAC solution in 1,1,2 TCE. The resulting coating solution contained 33.3% w/w drug on a dry, solid-only basis. Stents were coated by the method described in example 1. The dip-coated stents were spray coated twice with polymer-only solution as described in Example 6 (except ε-caprolactone-co-lactide was used as the copolymer). The final coated stents were designated as '33-C/L TC%'.

EXAMPLE 8

This example describes the results of testing the in vitro drug release of rapamycin from coated stent.

Figure 7:
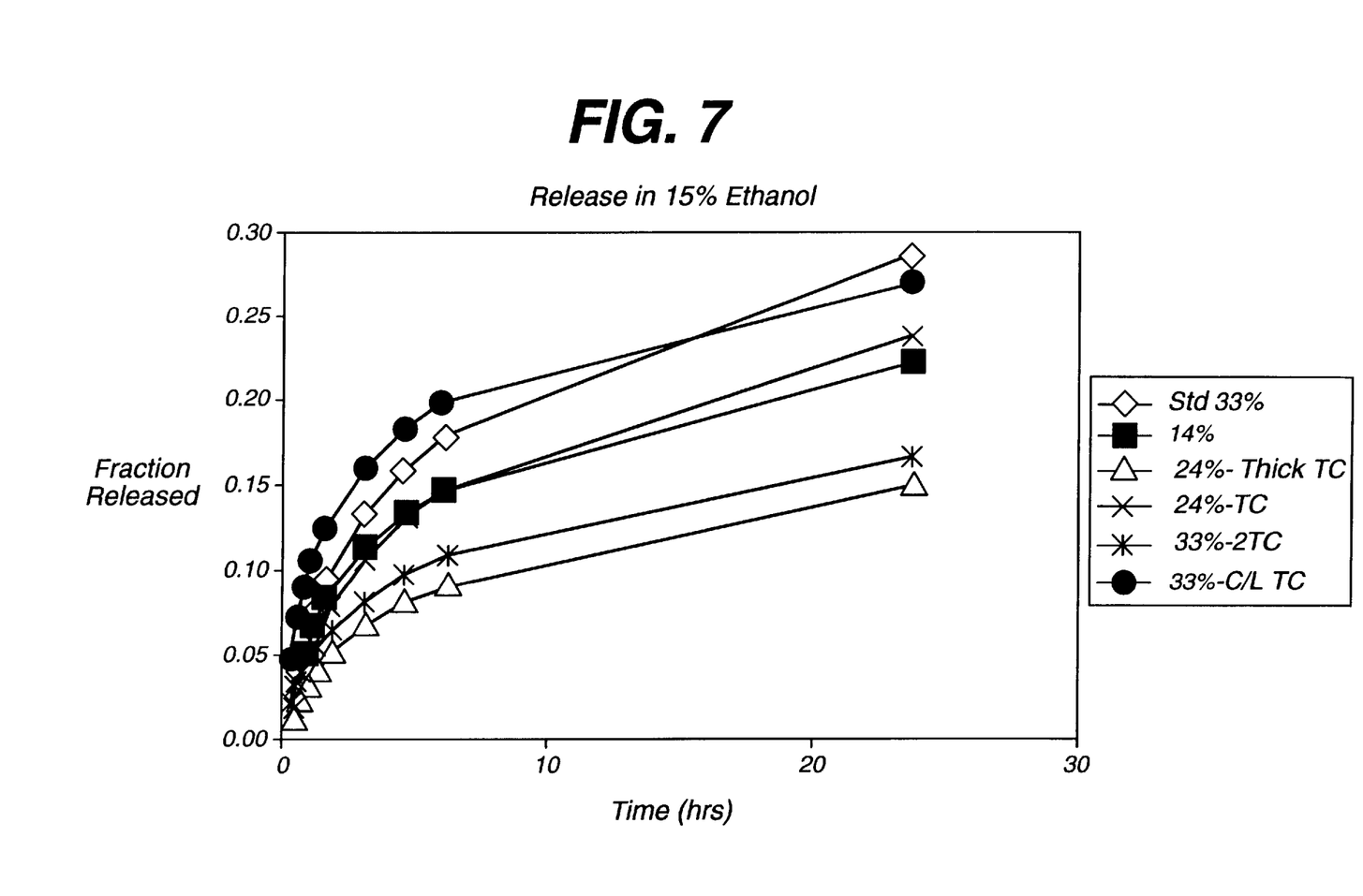
FIG. 7 is a graphical illustration of the in vitro release profile of a coated stent.
Figure 8:
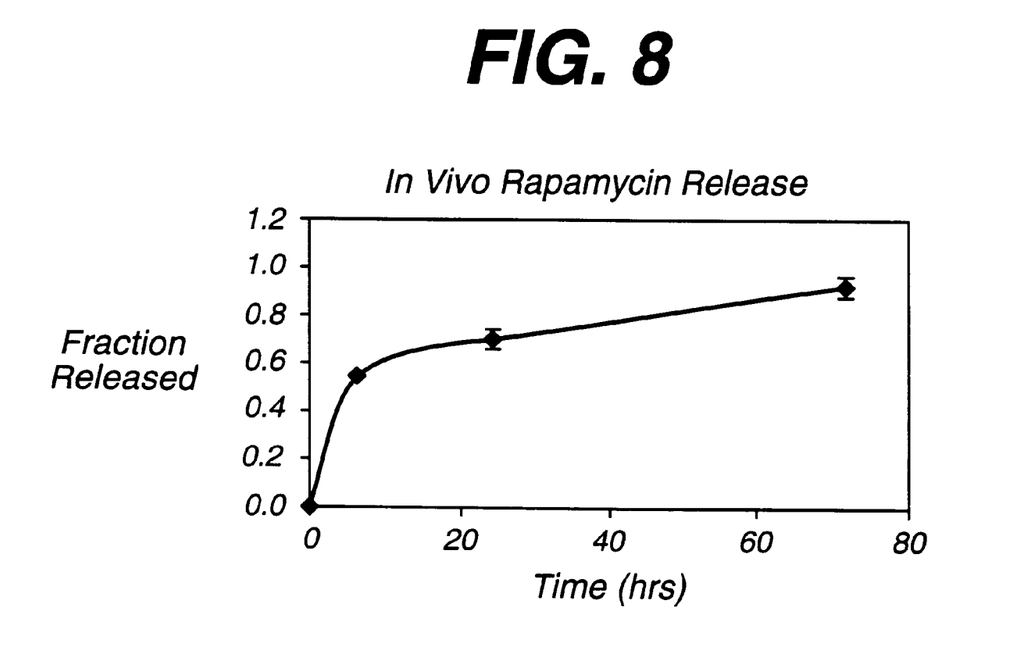
FIG. 8 is a graphical illustration of the in vivo release profile of a coated stent.

Coated stents were prepared as described in Example 7 with varying concentrations of rapamycin were tested for the in vitro release of rapamycin into an aqueous ethanol solution. As is indicated in FIG. 7, the stents denoted by the diamonds had a primer coating and a base coating that contained rapamycin. The total weight of the coating and rapamycin on the each stent was approximately 450 μg and contained 33 percent by weight of rapamycin. The coating was a copolymer of ε-caprolactone-co-glycolide (45:55 mole percent) applied by dip coating. The squares represent data points for stents having a primer coating and a base coating containing rapamycin. The total weight of the coating and drug was approximately 450 μg, which contained 14 percent by weight rapamycin. The coating material was also a copolymer of ε-caprolactone-co-glycolide (45:55 mole percent) applied by dip coating. The triangles represent data points for stents that had a primer coating and a base coating containing rapamycin. A primer coating and base coating (ε-caprolactone-co-glycolide 45:55 mole percent) were applied by dip coating the stent. A top coat of 200 μg (ε-caprolactone-co-glycolide 45:55 mole percent) was then applied using an ultrasonic spray device. The total weight of the coating and rapamycin was 650–700 μg, which contained 24 percent by weight rapamycin. The Xs represent data points for stents that had a primer coat and a base coating containing rapamycin. The primer coating and base coating (ε-caprolactone-co-glycolide 45:55 mole percent) were applied by dip coating the stent. A top coat of 100 μg (ε-caprolactone-co-glycolide 45:55 mole percent) was then applied using an ultrasonic spray device. The total weight of the coating and rapamycin was 550–600 μg, which contained 24 percent by weight rapamycin. The asterisk represents data points for stents that was coated with a primer, a base coat and two top coats. The primer coating and base coating (ε-caprolactone-co-glycolide 45:55 mole percent) were applied by dip coating the stents. A top coat of 100 μg (ε-caprolactone-co-glycolide; 45:55 mole percent) was then applied using an ultrasonic spray device. The total weight of the coating and rapamycin was approximately 550 μg, which contained 33 percent by weight rapamycin. The circles represent data points for stents that were dip coated with ε-caprolactone-co-lactide (40:60 mole percent). The stents were then top coated with an ultrasonic spray with approximately 100 μg of ε-caprolactone-co-lactide. The total coating weighed about 550 μg and contained 33 percent by weight rapamycin.

Each stent was placed in a 2.5 mL of release medium (aqueous ethanol; 15 percent by volume at room temperature) contained in a 13×100 mm culture tube. The tube was shaken in a water bath (INNOVA™ 3100; New Brunswick Scientific) at 200 rpm while maintaining ambient conditions. After a given time interval (ranging from 15 minutes to one day) the tubes were removed from the shaker and the respective stents carefully transferred to a fresh 2.5 ml Aliquot of release medium. The new tube was placed on the shaker and agitation resumed. A sample was removed from the aliquot, which had previously contained the stent and placed in a HPLC vial for determination of the rapamycin content by HPLC.

The HPLC system used to analyze the samples was a Waters Alliance with a PDA 996. This system is equipped with a photodiode array detector. 20 μL of each sample was withdrawn and analyzed on a $C_{18}$-reverse phase column (Waters Symmetry™ Column: 4.6 mm×100 mm $RP_{18}$ 3.5 μm with a matching guard column) using a mobile phase consisting of acetonitrile/methanol/water (38:34:28 v/v) delivered at a flow rate of 1.2 mL/min. The column was maintained at 60° C. through the analysis. Under these analytical conditions rapamycin had a retention time of 4.75±0.1 minutes. The concentration was determined from a standard curve of concentration versus response (area-under the curve) generated from rapamycin standards in the range of from 50 ng/mL to 50 μg/mL.

The results from testing the coated stents described above is shown in FIG. 7.

EXAMPLE 9

The goal of this study was to assess the rate of release of rapamycin from polymer-coated stents introduced in vivo into the coronary arteries of Yorkshire pigs. At various times after introduction of stents, the pigs were euthanized and the coronary arteries removed, the stents dissected free of the artery and analysed for rapamycin content using loading assay previously described. Through comparison with the amount of rapamycin contained on control, non-implanted stents, the in vivo rate of rapamycin release from the polymer coatings could be determined.

Experimental Procedure:

Male Yorkshire pigs weighing were used for these experiments. Animals were anesthetized with xylazine (2 mg/kg, IM), ketamine (17 mg/kg, IM) and atropine (0.02 mg/kg IM). Pigs were then intubated using standard procedure, and placed on flow-by oxygen with 1–2.5% volatile isoflurane for maintenance anesthesia via the endotracheal tube. Peripheral intravenous access was achieved by insertion of a 20 gauge Angiocath into the marginal ear vein; a 20 gauge arterial catheter was also placed in the ear for continuous blood pressure and heart rate monitoring.

To minimize the chance for clot formation at the stent site, animals were started on oral aspirin 325 mg per day three days prior to the planned procedure. Upon confirmation of adequate depth of anesthesia, the right inguinal region was shaved and sterilized, and sterilely draped. Aseptic technique was used throughout the remainder of the procedure. A linear incision parallel to the femoral vessels was made and the subcutaneous tissues dissected to the level of the artery. After adequate exposure, the femoral artery was isolated proximally with umbilical tape and distally with a 3.0 silk tie for hemostasis. Using surgical scissors, an arteriotomy was made, and an 8 Fr sheath inserted in the artery. Heparin 4,000 units and bretylium 75 mg were then administered intravenously after sheath insertion. Electrocardiogram, respiratory pattern, and hemodynamics were continuously monitored.

A hockey stick guiding catheter was inserted via the femoral sheath, and advanced to the left coronary ostium, whereupon left coronary cineangiography was performed. A single frame anteroposterior radiogram was developed, and the luminal diameters of the left anterior descending and circumflex arteries measured, in order to size the balloon-stent assembly for a prespecified balloon-to-artery ratio of approximately 1.1–1.2:1. Using guide catheter support and fluoroscopic guidance, a 0.014" guidewire was advanced into the lumen of the left anterior descending artery. Intracoronary stenting was performed by advancing a stent mounted on a conventional angioplasty balloon into position in the mid-portion of the left anterior descending artery. The stent was deployed by inflating the mounting balloon to 8 atmospheres for 30 seconds. Upon confirmation of vessel patency, the balloon and guidewire were removed from the left anterior descending artery, and the identical procedure was performed in the left circumflex artery. Upon completion of stent delivery in the left circumflex artery, the balloon and guidewire were withdrawn.

The guiding catheter and femoral arterial sheath were then removed, the femoral artery tied proximally with 3-0 silk suture for hemostasis and the inguinal incision was closed. After discontinuation of anesthesia, were returned to colony housing. Daily aspirin 325 mg was continued until euthanasia.

At various times after stent implantation, euthanasia was performed by overdose of pentobarbital administered IV. The chest was opened via a mid-sternal incision and the heart removed. Both the LAD and LCX were carefully dissected free of surrounding tissue. The stent was then dissected free of the arterial tissue and placed in a vial. The arterial tissue was frozen and stored for later analysis by HPLC.

FIG. 7 illustrates a typical in vivo release curve for a stent coating consisting of 33% rapamycin in polycaprolactone-co-glycolide.

EXAMPLE 10

This Example describes the in vivo testing of coated stents in a porcine coronary artery model.

This preliminary study was conducted to assess the ability of rapamycin released from $\epsilon$-caprolactone-co-glycolide copolymer-coated stents to inhibit intimal hyperplasia in vivo. Fourteen days after receiving rapamycin-loaded or control polymer coated stents, the male Yorkshire pigs were euthanized and the coronary arteries removed, the vessels prepared for histological evaluation and analysed for the amount of intimal growth. Through comparison control metal stents and stents containing polymer only, the in vivo ability of rapamycin to prevent neointimal growth could be determined.

Ethylene oxide-sterilized Palmaz-Schatz stents were implanted under sterile conditions in anesthetized farm pigs weighing 38 to 48 kg. Twenty-four hours prior to stent implantation, animals were given aspirin (325 mg, p.o., qd) and ticlopidine (250 mg, p.o., qd) to control chronic thrombosis; both aspirin and ticlopidine were continued daily until sacrifice. Anesthesia was induced with ketamine (20 mg/kg, i.m.), xylazine (2 mg/kg, i.m.) and sodium pentobarbital (10 mg/kg as needed) and maintained on 1–2% isofluorane in oxygen. An 8 Fr sheath was placed in an asceptically isolated left carotid artery and used subsequently to conduct either an 8 Fr JL 3.5 guide catheter for coronary angiography or to place a 0.014 inch guidewire for balloon delivery of stents to the appropriate coronary arteries. Heparin (150 unit/kg) was administered intraprocedurally to prevent acute thrombosis. Four experimental groups were employed; 1) metal stent control; 2) metal stent coated with 45/55 (w/w) $\epsilon$-caprolactone glycolide copolymer (CAP/GLY); 3) 32 $\mu$g rapamycin/stent formulated in CAP/GLY; 4) 166 $\mu$g rapamycin/stent formulated in CAP/GLY. Stents were deployed in both the LAD and LCX coronary arteries. Angiography was performed prior to, during, and immediately after stenting to both size the vessel for choice of balloon diameter (3.0, 3.5 or 4.0 mm) and to obtain measurements for determination of the balloon/artery ratio. Stents were deployed by inflating the delivery balloon to 8–10 ATM for 30 sec. Angiography was also performed at 14 days post-implantation to obtain final vessel diameter. Treatment groups were randomized and individual stents were implanted by an investigator who was blinded as to the treatment. However, only one treatment was employed in any given pig. Fourteen days after implantation, animals were killed, the vessels were perfusion fixed for 10 minutes at 100 mmHg with 10% formalin and then stored in 10% buffered formalin.

For histological assessment, the stented vessel was embedded in glycol methacrylate. Four 3–5 $\mu$m thick cross-sections taken at equal intervals along the length of the stent were placed on glass slides and prepared with Miller's Elastin stain. Histomorphometric measurements were determined in each section via microscopy and computerized image analysis. Individual values obtained for each vessel represent the average of the 4 measured sections. Differences between treatments were assessed by ANOVA and Dunnett's test.

TABLE 1

| Treatment | Histology | | Angiography | |
|---|---|---|---|---|
| | Intima/ Media ratio | Intimal Area (mm$^2$) | % Diameter Stenosis | B/A Ratio |
| Metal Control (n = 10) | 0.90 ± 0.05 | 3.65 ± 0.82 | 24.8 ± 3.9[1] | 1.27 ± 0.05 |
| CAP/GLY (n = 8) | 0.91 ± 0.11 | 4.15 ± 0.23 | 38.0 ± 4.0 | 1.32 ± 0.04 |
| CAP/GLY + 32 $\mu$g rapamycin (n = 10) | 0.75 ± 0.04 | 3.27 ± 0.16 | 21.6 ± 3.6[1] | 1.23 ± 0.03 |
| CAP/GLY + 166 $\mu$g rapamycin (n = 8) | 0.65 ± 0.04[1,2] | 2.87 ± 0.31 | 23.9 ± 2.3[1] | 1.27 ± 0.05 |

[1]p < 0.05 from CAP/GLY
[2]p < 0.05 from Metal Control
All values are mean ± sem. B/A ratio = balloon to artery ratio, an index of the consistency of stent expansion from group to group As can be seen in Table 1, local delivery of rapamycin to injured coronary arteries resulted in a significant (p<0.05) reduction in intima:media ratio in the 166 $\mu$g treatment group and a small but non-significant reduction in the 32 $\mu$g treatment group when compared with the polymer and bare metal control groups. Rapamycin delivered from the GAP/GLY coating also resulted in non-significant dose-related decreases in neointimal area in both the 32 $\mu$g and 166 $\mu$g treatment groups. The percent diameter stenosis as assessed by angiography was also significantly reduced in the 2 rapamycin treatment groups when compared to the CAP/GLY group, although the reduction in this parameter from the metal control was small and non-significant. Never-the-less, in this preliminary 14 day study, these data suggest that local release of rapamycin from a biodegradable hydrophobic polymer coating may be capable of limiting the amount of neointimal proliferation which occurs as a result of stent deployment.

EXAMPLE 11

In the glove box, 100 $\mu$L (33 $\mu$mol) of a 0.33 M stannous octoate solution in toluene, 115 $\mu$L (1.2 mmol) of diethylene glycol, 24.6 grams (170 mmol) of L-lactide, and 45.7 grams (400 mmol) of $\epsilon$-caprolactone were transferred into a silanized, flame dried, two neck, 250 mL round bottom flask equipped with a stainless steel mechanical stirrer and a nitrogen gas blanket. The reaction flask was placed in an oil bath already set at 190° C. and held there. Meanwhile, in the glove box, 62.0 grams (430 mmol) L-lactide were transferred into a flame dried, pressure equalizing addition funnel. The funnel was wrapped with heat tape and attached to the second neck of the reaction flask. After 6 hours at 190° C., the molten L-lactide was added to the reaction flask over 5 minutes. The reaction was continued overnight for a total reaction time of 24 hours at 190° C. The reaction was allowed to cool to room temperature overnight. The copolymer was isolated from the reaction flask by freezing in liquid nitrogen and breaking the glass. Any remaining glass fragments were removed from the copolymer using a bench grinder. The copolymer was again frozen with liquid nitrogen and broken off the mechanical stirring paddle. The copolymer was ground into a tared glass jar using a Wiley Mill and allowed to warm to room temperature in a vacuum oven overnight. 103.13 grams of 40:60 poly($\epsilon$-caprolactone-co-L-lactide) were added to a tared aluminum pan and then devolitilized under vacuum at 110° C. for 54 hours. 98.7 grams (95.7% by weight) of copolymer were recovered after devolitilization.

We claim:

1. A method for coating a stent having an outer surface and inner surface with passages between the outer surface and inner surfaces comprising:
    (a) contacting the stent with a liquid coating solution containing a film forming biocompatible polymer under conditions suitable to allow the film forming biocompatible polymer to coat at least one surface of the stent;
    (b) before the coating solution dries creating fluid movement out of the passages of the stent sufficient to prevent the film forming biocompatible polymers from substantially blocking said passages thereafter;
    (c) drying the stent to provide at least a partially coated stent with a first coating
wherein said fluid movement is created by contacting a mandrel with the inner surface of the stent and moving the mandrel relative to the stent to prevent bridges from forming in said passages.

2. The method of claim 1 wherein the stent is contacted with the coating solution by dipping the stent into the coating solution.

3. The method of claim 1 wherein the stent is contacted with the coating solution by spraying the coating solution on to the stent.

4. The method of claim 2 wherein fluid movement is created by contacting the outer surface of the stent with the inner surface of a tube and moving the tube relative to the stent to prevent bridges from forming in said passages.

5. The method of claim 3 wherein fluid movement is created by contacting the outer surface of the stent with the inner surface of a tube and moving the tube relative to the stent to prevent bridges from forming in said passages.

6. The method of claim 1 wherein the film forming biocompatible polymer is selected from the group consisting of aliphatic polyesters, poly(amino acids), copoly(ether-esters), polyalkylenes oxalates, polyamides, poly(iminocarbonates), polyorthoesters, polyoxaesters, polyamidoesters, polyoxaesters containing amido groups, poly(anhydrides), polyphosphazenes, biomolecules and blends thereof.

7. The method of claim 1 wherein the film forming polymer is a biocompatible aliphatic polyester.

8. The method of claim 7 wherein the film forming polymer is an elastomeric, biocompatible aliphatic polyester.

9. The method of claim 8 wherein the elastomeric, bicompatible aliphatic polyester is selected from the group consisting of elastomeric copolymers of $\epsilon$-caprolactone and glycolide, elastomeric copolymers of $\epsilon$-caprolactone and lactide, elastomeric copolymers of p-dioxanone and lactide, elastomeric copolymers of $\epsilon$-caprolactone and p-dioxanone, elastomeric copolymers of p-dioxanone and trimethylene carbonate, elastomeric copolymers of trimethylene carbonate and glycolide, elastomeric copolymer of trimethylene carbonate and lactide and blends thereof.

10. The method of claim 1 wherein additionally contained in the coating solution is a pharmaceutically active compound.

11. The method of claim 10 wherein the pharmaceutically active compound is selected from the group consisting of antiproliferative/antimitotic agents, antibiotics, enzymes, antiproliferative/antimitotic alkylating agents, antiproliferative/antimitotic antimetabolites; hormones; anticoaglants; fibrinolytic agents; antiplatelet agents; antimigratory agents; antisecretory agents; antiinflammatory agents; immunosuppressive agents; angiogenic agents; nitric oxide donors; anti-sense olgio nucleotides and combinations thereof.

12. The method of claim 11 wherein the pharmaceutically active compound is rapamycin.

13. The method of claim 1 wherein after the stent is dried a second coating is applied.

14. The method of claim 13 wherein the second coating is applied by spraying a solution containing a film forming biocompatible polymer onto at least one surface of the stent.

15. The method of claim 13 wherein the second coating contains a film forming biocompatible polymer not present in the first coating.

16. A method for coating a tubular stent having a first surface and second surface with passages between the first surface and second surfaces comprising;
    (a) placing the tubular stent on a mandrel; then
    (b) contacting the stent and mandrel with a liquid coating solution containing a film forming biocompatible polymer under conditions suitable to allow the film forming biocompatible polymer to coat at least one surface of the stent while moving the stent relative to the mandrel to cause fluid flow through said passages sufficient to prevent the film forming biocompatible polymer from substantially blocking said passages; thereafter
    (c) drying the stent to provide at least a partially coated tubular stent with a first coating.

17. The method of claim 16 wherein the film forming biocompatible polymer is selected from the group consisting of of aliphatic polyesters, poly(amino acids), copoly(ether-esters), polyalkylenes oxalates, polyamides, poly(iminocarbonates), polyorthoesters, polyoxaesters, polyamidoesters, polyoxaesters containing amido groups, poly(anhydrides), polyphosphazenes, biomolecules and blends thereof.

18. The method of claim 16 wherein the stent is coated with an elastomeric aliphatic polyester.

19. The method of claim 18 wherein the elastomeric, bicompatible aliphatic polyester is selected from the group consisting of elastomeric copolymers of $\epsilon$-caprolactone and glycolide, elastomeric copolymers of $\epsilon$-caprolactone and lactide, elastomeric copolymers of p-dioxanone and lactide, elastomeric copolymers of $\epsilon$-caprolactone and p-dioxanone, elastomeric copolymers of p-dioxanone and trimethylene carbonate, elastomeric copolymers of trimethylene carbonate and glycolide, elastomeric copolymer of trimethylene carbonate and lactide and blends thereof.

20. The method of claim 19 wherein the elasomertic polyester is $\epsilon$-caprolactone-co-glycolide.

21. The method of claim 20 wherein a second coating is applied.

22. The method of claim 21 wherein the first coating is $\epsilon$-caprolactone-co-glycolide and the second coating is $\epsilon$-caprolactone-co-glycolide.

23. The method of claim 22 wherein the first coating contains a pharmaceutically active compound.

24. The method of claim 19 wherein the elasomertic polyester is $\epsilon$-caprolactone-co-lactide.

25. The method of claim 24 wherein a second coating is applied.

26. The method of claim 25 wherein the first coating is ε-caprolactone-co-lactide and the second coating is ε-caprolactone-co-lactide.

27. The method of claim 25 wherein the first coating is ε-caprolactone-co-lactide and the second coating is ε-caprolactone-co-glycolide.

28. The method of claim 26 wherein the first coating contains a pharmaceutically active compound.

29. The method of claim 27 wherein the first coating contains a pharmaceutically active compound.

30. The method of claim 26 wherein the pharmaceutically active compound is rapamycin.

31. The method of claim 27 wherein the pharmaceutically active compound is rapamycin.

32. The method of claim 6 wherein additionally present is a biocompatible hydrophilic polymer.

33. The method of claim 31 wherein the biocompatible hydrophilic polymer is selected from the group consisting of polyethylene oxide, polyvinyl pyrrolidone, polyethylene glycol, carboxylmethyl cellulose, hydroxymethyl cellulose and combination thereof.

34. The method of claim 25 wherein the second coating is a coating applied to modulate the release rate of the pharmaceutical agent in the first coating.

35. The method of claim 34 wherein the second coating weights between about 10 micrograms and about 2000 micrograms.

36. The method of claim 34 wherein the second coating weights between about 100 micrograms and about 1700 micrograms.

37. The method of claim 21 wherein additionally present are at least two top coats.

38. The method of claim 21 wherein additionally present are at least three top coats.

* * * * *